United States Patent [19]

Pascal et al.

[11] 4,233,463

[45] Nov. 11, 1980

[54] PROCESS FOR THE SEPARATION OF 2,4-DINITRO-6-T-BUTYL-3-METHYLANISOLE, REFERRED TO AS MUSK AMBRETTE, FROM THE CRUDE SYNTHESIS MIXTURES IN WHICH IT IS PRESENT

[75] Inventors: Hélène M. Pascal, Le Pontet; Jean-Marie L. Emeury, Sorgues, both of France

[73] Assignee: Societe Nationale des Poudres et Explosifs, Paris, France

[21] Appl. No.: 970,131

[22] Filed: Dec. 18, 1978

[30] Foreign Application Priority Data

Dec. 29, 1977 [FR]  France ............................. 77 39624

[51] Int. Cl.³ ............................................. C07C 79/35
[52] U.S. Cl. ................................................... 568/584
[58] Field of Search ........................................ 568/584

[56] References Cited

U.S. PATENT DOCUMENTS

| | | | |
|---|---|---|---|
| 481,685 | 8/1892 | Bauer | 568/584 |
| 1,875,916 | 9/1932 | Clemmenson | 568/584 |
| 1,926,080 | 9/1933 | Borman | 568/584 |
| 2,007,234 | 7/1935 | Wirth | 568/584 |
| 2,476,815 | 7/1949 | Carpenter et al. | 568/584 |
| 2,493,797 | 1/1950 | Wood | 568/584 |

FOREIGN PATENT DOCUMENTS

10946 of 1895 United Kingdom ................... 568/584

OTHER PUBLICATIONS

Carpenter et al., Jour. of Org. Chemistry, vol. 16, (1951), 586–620.

*Primary Examiner*—Bernard Helfin
*Attorney, Agent, or Firm*—Bucknam and Archer

[57] ABSTRACT

The invention relates to a process for the separation of 2,4-dinitro-6-t-butyl-3-methylanisole, referred to as musk ambrette, from the crude mixtures in which it is present, which are obtained by nitrating 6-t-butyl-3-methylanisole.

According to the invention, an amount of water representing from 5 to 40% by weight of the nitrating mixture used in the synthesis is introduced onto the crude synthesis mixture in a first addition, the pure musk ambrette obtained is collected and several small amounts of water, representing from 1 to 15% by weight of the said nitrating mixture used, are then introduced, the precipitated product being collected between each addition. The process makes it possible to collect, in a pure form and without the use of an organic extraction solvent, about three quarters of the musk ambrette present in the crude synthesis mixture.

5 Claims, No Drawings

PROCESS FOR THE SEPARATION OF 2,4-DINITRO-6-T-BUTYL-3-METHYLANISOLE, REFERRED TO AS MUSK AMBRETTE, FROM THE CRUDE SYNTHESIS MIXTURES IN WHICH IT IS PRESENT

The present invention relates to a process for the separation of 2,4-dinitro-6-tert.-butyl-3-methylanisole, referred to as musk ambrette, from the crude mixtures in which it is present, which are obtained by nitrating 6-t-butyl-3-methylanisole.

A common feature of modern processes for the manufacture of musk ambrette is the use of the material 6-t-butyl-3-methylanisole.

The nitration of this latter substance, in two stages or, more generally, in a single stage, leads to a crude synthesis mixture which mainly contains musk ambrette but also contains unreacted 6-t-butyl-3-methylanisole, mononitro-6-t-butyl-3-methylanisole, 2,4-dinitro-3-methylanisole, the residue from the nitrating mixture and other poorly identified organic products which are generally coloured and in small proportions.

As far as is known, the separation of musk ambrette from the crude synthesis mixtures in which it is present has hitherto been achieved in only one way which consists in pouring the said mixtures onto ice or a mixture of water and ice.

In this manner, the said crude synthesis mixtures are subjected to a kind of soaking, whilst all the organic substances separate out and the constituents of the residue from the nitrating mixture pass into dilute solution in the aqueous phase.

This separation process is illustrated, for example, in the article by CARPENTER et al., page 603, which appeared in the Journal of Organic Chemistry, volume 16, No. 4, of 1951 and in the article by GEL'PERIN et al., page 438, which appeared in Zhur. Vsesojuz Khim. Obshchestva im. D. I. Mendeleeva (1960), 5 (Chemical Abstracts 55:908 i).

However, this process is far from satisfactory. In fact, the aqueous phase thus recovered contains a highly dilute nitrating mixture which therefore requires very considerable concentration before it can optionally be re-used, whilst the organic phase consists of a mixture of substances of similar chemical structures, in which musk ambrette is rarely present to the extent of more than 80%.

Consequently, if it is desired to obtain a musk ambrette which is of high purity (melting point greater than about 83° C.) or free from certain disadvantageous impurities (for example colorising quinone impurities), it is necessary to extract the musk ambrette from the said organic phase using an organic solvent and then to wash and neutralise this extract.

This extraction, which is generally carried out using benzene and hexane, and the ensuing treatment raise the manufacturing costs of the musk ambrette. Furthermore, in addition to the evaporation of the solvent, which this extraction involves, there is also the need to carry out several clearing operations with methanol, or even several recrystallisations, before obtaining a pure product which is free from coloration.

Applicants have now discovered a process for the separation of musk ambrette, having a high degree of purity, from the crude synthesis mixtures obtained by nitrating 6-t-butyl-3-methylanisole, which furthermore makes it possible to separate off virtually all the impurities inherent in this type of process, whilst facilitating the recycling of the constituents of the nitrating mixture.

The process according to the invention is characterised in that water is introduced into the crude synthesis mixture in the amount of at least 5% and at most 200% by weight of the nitrating mixture used in the process, in one or more additions, each addition containing nor more than 100% by weight of the said nitrating mixture, and in that, after each introduction, the precipitated product is separated off.

According to a first variant of the invention, the water is introduced in a first addition which represents from 25 to 100% of the weight of the nitrating mixture used, the product which has precipitated is separated off and, optionally, further water is introduced in a second addition which represents from 100 to 175% by weight of the said nitrating mixture used.

According to a second variant of the invention, the water is introduced in a first addition which represents from 5 to 40% by weight of the nitrating mixture used, the pure mask ambrette obtained is collected and several small amounts of water, representing from 1 to 15% by weight of the said nitrating mixture used, are then introduced, the precipitated product being collected between each addition. Optionally, the separation according to this variant is terminated by introducing, all at once, the amount of water which is required to bring the total amount of water introduced into the crude synthesis mixture to between 100 and 200% by weight of the said nitrating mixture used.

The process according to the invention is applied especially to the crude synthesis mixtures obtained by the processes consisting in nitrating 6-t-butyl-3-methylanisole, in one or two stages, using a nitrating mixture initially comprising nitric acid, acetic anhydride and optionally acetic acid. This is to be understood as meaning that the nitrating mixture can initially contain either concentrated nitric acid, acetic anhydride and a few percent of acetic acid formed by reaction of the acetic anhydride with the water in the nitric acid used (which generally contains about 2% thereof), or concentrated nitric acid, acetic anhydride and acetic acid which has been intentionally added.

The crude synthesis mixtures are generally produced at a temperature between −15° and +25° C. However, it has been observed that the separation by the process according to the invention takes place particularly satisfactorily if the temperature of the mixture which is to receive water is brought to between about 15° and 20° C., before each amount of water is introduced, these introductions preferably being carried out slowly and whilst stirring.

Finally, once each introduction of water has ended, it is advantageous to stir the medium moderately for a few minutes before recovering the precipitated product using any known means. For the last precipitation, it is preferred to stir the medium for 15 to 45 minutes before separating off the precipitate, so that the latter contains virtually all the aromatic substances which still remain in the medium.

It has been found that, surprisingly for those skilled in the art, if the first abovementioned variant of the process according to the invention is applied, from 45 to 70% of the musk ambrette which can theoretically be produced by the process is successfully recovered, with a purity which satisfies most of the commercial requirements (melting point ≧83° C.), which is equivalent to recovering the major part of the musk which is in fact contained in the crude synthesis mixture, in a particularly valuable form.

It has also been found that, if the second variant of the process according to the invention is applied, the first introduction of water (5 to 40% by weight of the nitrating mixture used) results in the production of 40 to 65% of the musk ambrette which can theoretically be produced, with an excellent purity since the melting point of the musk is between 83° and 85° C. and generally about 84° C.

It should be noted that the yield of the separating operation according to the invention depends on the operating conditions of the nitrating process used (essentially the composition of the nitrating mixture, the nitrating ratio and the temperature) and that it is not of course possible to separate off more product than has been synthesised. It is therefore particularly recommended to use, as the nitrating process, the process described in a patent application filed on the same day as the present application, which fundamentally consists in using a ternary nitrating mixture preferably containing from 30 to 50% of acetic acid, from 20 to 30% of acetic anhydride and from 25 to 45% by weight of nitric acid, with a nitrating ratio of between 5 to 6, at a temperature between −5° and 30° C. and preferably between 7° and 15° C.

The yield of the separating process according to the invention is particularly good as regards the musk ambrette, since it is considered that more than 90% of the musk contained in the medium is recovered after having introduced, into the crude synthesis mixture, an amount of water having an equal mass to that of the nitrating mixture used in the synthesis, and that there is no longer any musk in the aqueous phase after the introduction of 200% of water, relative to the said nitrating mixture.

However, a particularly valuable feature, according to the invention, is that it is now possible to produce musk ambrette of various grades in an extremely simple manner, with a yield which can be chosen within a wide range. Thus, if it is desired to obtain very pure musk ambrette from a given crude synthesis mixture, the second abovementioned variant is applied, a smaller amount of water being introduced, the greater is the desired purity of the musk. Once this operation has been carried out, it is still possible to obtain musk of satisfactory commercial purity by introducing a further amount of water, this amount being greater, the greater is the desired yield of this grade, and being smaller, the greater is the desired degree of purity. On the other hand, if it is desired to obtain directly a high yield of musk ambrette of ordinary commercial grade, it is recommended to use the first abovementioned variant.

A further predominant advantage of the process according to the invention is that it is not necessary to take up an organic phase in an organic solvent as in the former processes. In fact, the musk obtained by the process according to the invention is in the form of a solid, whereby a simple clearing operation using a volatile alcohol makes it possible, in the event of strict requirements, to further purify and to decolorise the said musk.

In summary, the separating process according to the invention makes it possible to avoid the usual constraints by employing simple means of operation and to separate off the musk ambrette with good yields, not only from the mixture used for its nitration, but also from the by-products of similar chemical structure which accompany it.

Further advantages of the process according to the invention will become apparent in the following examples which are given by way of an illustration of the invention but in no way limit the scope thereof.

EXAMPLE 1

840 g of a sediment consisting of 49% of acetic acid, 31% of acetic anhydride and 20% of concentrated nitric acid (containing 98% of $HNO_3$) were prepared. The temperature of this nitrating premixture was brought to 10° C. and kept at this value and 178 g of 3-methyl-6-t-butylanisole and 160 g of concentrated nitric acid were introduced simultaneously in the course of one hour, whilst stirring.

After the introduction, the reaction medium was stirred moderately for one hour at 25° C. and 250 ml of water (25% by weight of the total nitrating mixture) were introduced thereto.

A precipitate of musk ambrette was observed. 140 g (52% of theory) of pure musk, having a melting point of 85° C., were thus recovered.

A second addition of 100 ml of water made it possible to collect 58 g of musk having a melting point of 73° C.

A third addition of 100 ml gave a further 12 g of product having a melting point of 72° C., and a final addition of 1,000 ml of water gave 24 g of product containing only 30% of musk.

Analysis of the crude synthesis mixture showed that it contained an amount of musk corresponding to 72% of the theoretical yield.

The process according to the invention therefore made it possible to recover 73% of the musk present in the medium, in a very pure form.

EXAMPLE 2

A sediment consisting of 104 g of acetic anhydride was prepared. The temperature was kept at −15° C. and a solution of 60 g of 6-t-butyl-3-methylanisole in 130 g of acetic anhydride, and 130 g of concentrated nitric acid (containing 98% of $HNO_3$), were simultaneously introduced into the reactor.

The introduction had ended after 90 minutes. The medium was stirred for a further 45 minutes at −12° C. in order to allow the reaction to proceed to completion.

The temperature of the crude synthesis mixture was brought back to 0° C. and 100 ml of water were introduced in a first addition.

46 g of a precipitate of musk ambrette, melting at 83° C. and free from quinone products and dinitromethylanisole, were recovered, that is to say 50% of the theoretical amount of musk and 74% of the musk which was in fact present in the crude synthesis mixture.

The temperature, which rose to 20° C. on the introduction of the first amount, was maintained and four amounts of water, each of 65 ml, were successively introduced, whilst stirring the medium for a few minutes in order to complete the precipitations and filtering the medium after each precipitation.

The second addition yielded a further 17 g of product containing 70% of musk ambrette, so that more than 90% of the musk ambrette present in the crude mixture had been recovered at this stage in forms which could be used directly in industry. The following additions yielded precipitates essentially consisting of 2,4-dinitro-3-methylanisole.

EXAMPLE 3

A crude synthesis mixture identical to that obtained in Example 1 was treated in accordance with the first variant of the process according to the invention.

To do this, 300 ml of water (30% by weight of the nitrating mixture used overall) were introduced into the said mixture which had been brought to 18° C.

166 g of a precipitate of pure musk ambrette, melting at 84° C., were collected, which corresponds to 62% of the stoichiometric amount and 90% of the musk contained in the crude synthesis mixture.

1,000 ml of water were then introduced into the filtrate and 60 g of an impure solid product containing 30% of musk were collected.

EXAMPLE 4

The experiment of Example 3 was repeated, but the first addition consisted of 330 ml of water.

185 g of a precipitate of musk ambrette, containing more than 99% of musk ambrette and melting at 84° C., were collected, which corresponds to a yield of 69%, relative to the theoretical amount, and represents 95% of the total musk contained in the crude synthesis mixture.

EXAMPLE 5

A crude synthesis mixture identical to that of Examples 3 and 4 was treated in accordance with the second variant of the process according to the invention.

The medium was kept at 18° C. and 280 ml of water were introduced thereto, after which the mixture was stirred for 30 minutes. This yielded 182 g of a precipitate of very pure musk ambrette, melting at 85° C., that is to say a yield of 61%, relative to the stoichiometric amount.

110 ml of water were run into the above filtrate and a further 65 g of product, melting at 73° C. and containing 65% of musk, were collected.

A further 110 ml of water were run in and 13 g of an impure precipitate were collected in the same manner.

Finally, 1,500 ml of water were run onto the resulting filtrate and a further 27 g of product, containing only 30% of musk and 70% of 4,6-dinitro-3-methylanisole, were extracted.

The overall yield of musk from the reaction was 81% and three quarters of the musk contained in the crude synthesis mixture was therefore collected in the form of a very pure product.

EXAMPLE 6

A kilogram of sediment, consisting of 40% of acetic acid, 28% of acetic anhydride and 32% of 98% strength nitric acid, was prepared.

The temperature of the medium was kept at 25° C., using a brine bath, and 178 g of 6-t-butyl-3-methylanisole were run into this nitrating bath in the course of 1 hour, whilst stirring.

The reaction medium was kept at 25° C. for half an hour once the introduction had ended. The mixture obtained was then poured onto a mixture of water and ice. The organic phase was taken up in 1,500 ml of hexane and, after evaporation off the solvent, 262 g of a product having a melting point of 64° C. and containing 80% of musk ambrette were collected. The yield of this product is therefore 76%, but the product is of very mediocre grade, despite the use of the organic extraction solvent.

We claim:

1. Process for the separation of 2,4-dinitro-6-t-butyl-3-methylanisole from the crude reaction mixtures obtained by nitrating 6-t-butyl-3-methylanisole by reaction with a mixture of nitric acid and acetic anhydride wherein water is introduced into the crude reaction mixture in the amount of at least 5% and at most 200% by weight of the nitrating mixture used in the process, in at least two additions, each addition of water containing no more than 100% by weight of the said nitrating mixture, and prior to each introduction of water, the precipitated product is separated off.

2. Separation process according to claim 1, wherein the water is introduced in a first addition which represents from 25 to 100% of the weight of the nitrating mixture, the product which has precipitated is separated off and, further water is introduced in a second addition which represents from 100 by 175% by weight of the said nitrating mixture used.

3. Separation process according to claim 1, wherein the water is introduced in a first addition which represents from 5 to 40% by weight of the nitrating mixture used, the pure 2,4-dinitro-6-butyl-3-methylanisole obtained is collected and several small amounts of water, each representing from 1 to 15% by weight of the said nitrating mixture used are then introduced, the precipitated product being collected between each addition.

4. Separation process according to claim 2, wherein before each amount of water is introduced, the mixture which is to receive water is brought to a temperature between 15° and 20° C.

5. Separation process according to claim 2, wherein after each amount of water has been introduced, the medium is stirred moderately for several minutes before recovering the precipitated product.

* * * * *